(12) United States Patent
Mizumo

(10) Patent No.: US 7,252,634 B2
(45) Date of Patent: Aug. 7, 2007

(54) CONFOCAL PROBE HAVING SCANNING MIRRORS MOUNTED TO A TRANSPARENT SUBSTRATE IN AN OPTICAL PATH OF THE PROBE

(75) Inventor: Rogerio Jun Mizumo, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 361 days.

(21) Appl. No.: 10/699,699

(22) Filed: Nov. 4, 2003

(65) Prior Publication Data

US 2004/0122289 A1    Jun. 24, 2004

(30) Foreign Application Priority Data

Nov. 5, 2002   (JP)   ............................. 2002-321322
Nov. 5, 2002   (JP)   ............................. 2002-321323

(51) Int. Cl.
*A61B 1/06*     (2006.01)
*G02B 26/08*    (2006.01)
(52) U.S. Cl. ...................................... 600/160; 359/202
(58) Field of Classification Search ........ 356/201–202, 356/212, 214; 600/108–109, 160, 182
See application file for complete search history.

(56) References Cited

U.S. PATENT DOCUMENTS

| 4,174,154 | A   | 11/1979 | Kawasaki ................... 359/861 |
| 5,120,953 | A   | 6/1992  | Harris ...................... 250/227.2 |
| 5,161,053 | A   | 11/1992 | Dabbs ........................ 359/384 |
| 5,323,009 | A   | 6/1994  | Harris ....................... 250/458.1 |
| 5,606,447 | A   | 2/1997  | Asada et al. ................ 359/199 |
| 5,742,419 | A   | 4/1998  | Dickensheets et al. ...... 359/201 |
| 5,767,666 | A   | 6/1998  | Asada et al. ................... 324/97 |
| 5,812,727 | A   | 9/1998  | Kanazawa et al. ........... 385/137 |
| 6,371,909 | B1* | 4/2002  | Hoeg et al. .................. 600/173 |
| 6,477,403 | B1  | 11/2002 | Eguchi et al. .............. 600/478 |
| 6,485,413 | B1* | 11/2002 | Boppart et al. ............. 600/160 |
| 2003/0233028 | A1* | 12/2003 | Tokuda et al. ............. 600/160 |
| 2004/0181148 | A1* | 9/2004  | Uchiyama et al. .......... 600/425 |

FOREIGN PATENT DOCUMENTS

| JP | HEI 3-197909 | 8/1991 |
| JP | HEI 5-6564   | 1/1993 |
| JP | HEI 5-107428 | 4/1993 |
| JP | HEI 6-94947  | 4/1994 |
| JP | 9-98945      | 4/1997 |
| JP | 2000-46554   | 2/2000 |
| JP | 3032720      | 2/2000 |
| JP | 3052150      | 4/2000 |
| JP | 2001-305382  | 10/2001 |
| JP | 2002-286977  | 10/2002 |

* cited by examiner

*Primary Examiner*—John Leubecker
*Assistant Examiner*—Philip R Smith
(74) *Attorney, Agent, or Firm*—Greenblum & Bernstein, P.L.C.

(57) ABSTRACT

A confocal probe unit is provided with a scanning type confocal probe, which includes at least one scanning mirror, and a transparent substrate on which the at least one scanning mirror is mounted. The transparent substrate is inserted in an optical path of the confocal probe such that a light beam proceeding along the optical path is deflected by the scanning mirror.

16 Claims, 5 Drawing Sheets

CONFOCAL PROBE HAVING SCANNING MIRRORS MOUNTED TO A TRANSPARENT SUBSTRATE IN AN OPTICAL PATH OF THE PROBE

The present disclosure relates to the subject matters contained in Japanese Patent Application No. 2002-321322 and No. 2002-321323, both filed on Nov. 5, 2002, which are expressly incorporated herein by reference in their entireties.

BACKGROUND OF THE INVENTION

The present invention relates to a confocal probe to be employed in an endoscope device and a confocal endoscope device for observing tissues inside the human body and the like.

Conventionally, when tissues of a human body are examined, parts of the tissues are cut using a treatment tool such as a forceps for cutting. Then, the cut parts of the tissues are examined. Such an examination requires a relatively long time, and it has been difficult to apply medical treatment quickly.

Recently, a confocal optical scanning probe for non-invasive imaging has been known. Typically, the confocal probe is configured to illuminate tissues inside a human body with a scanning laser beam, and receives a reflected beam that is reflected at a focal point of an objective optical system of the confocal probe. Examples of such a confocal probe are disclosed in Japanese Patent No. 3032720 and No. 3052150.

The confocal probe is configured such that a pin hole is provided, in front of a detector, at a position conjugate with an object-side focal point of the objective optical system. With this configuration, the detector only receives the reflected light, which is reflected by the tissues, at a point on which the light is focused. The detector, which is connected to an image processing unit, receives the reflected light passed through the pin hole, and performs photoelectric transformation.

In order to capture two-dimensional or three-dimensional images of the tissues, the laser beam is scanned on the tissues. For this purpose, the confocal probe is provided with scanning mirrors for scanning the laser beam along two-dimensional directions, or along three-dimensional directions.

Each of the scanning mirrors employed in the confocal probe is formed on semi-conductive material such as a silicon substrate. In a conventional confocal probe, the silicon substrate mounting the scanning mirror is typically secured inside a device with supporting members secured on an inner wall of a main body of the device.

As above, the supporting members are located on an outer side of the scanning mirror (i.e., apart from the optical axis of the probe), in which case, the diameter of the probe tends to be larger. Further, in conventional confocal probes, a plurality of mirrors for scanning a beam in different directions are formed on different silicon substrates. Therefore, the manufacturing process of the scanning mirrors and assembling process thereof tends to be complicated, which may increase manufacturing costs.

The scanning optical system is generally made of glass material such as BK7 or quart glass. The CTE (coefficient of thermal expansion) of the silicon substrate is several ten of times as much as the CTE of the BK7 or quart glass. Therefore, when a relatively large thermal change occurs, a positional relationship of the optical system and the scanning mirrors is shifted, which causes the optical path of the scanning laser beam to be displaced. Due to this relatively worse thermal characteristic of the probe, under a relatively high temperature around the probe, it is difficult to keep a precise location of the image.

SUMMARY OF THE INVENTION

The present invention is advantageous in that a relatively small diameter of a confocal probe can be realized, manufacturing and assembling process can be simplified, and a confocal probe having excellent thermal characteristics can be provided.

According to an aspect of the invention, there is provided a scanning type confocal probe, which is provided with at least one scanning mirror, and a transparent substrate on which the at least one scanning mirror is mounted. The transparent substrate is inserted in an optical path of the confocal probe such that a light beam passing along the optical path is deflected by the at least one scanning mirror.

Optionally, the scanning type confocal probe includes a first scanning mirror that deflects the light beam in a first predetermined direction, and a second scanning mirror that deflects the light beam in a second predetermined direction which is perpendicular to the first predetermined direction. In a particular case, the first scanning mirror and the second scanning mirror may be mounted on the same transparent substrate.

Alternatively, the scanning type confocal probe includes a scanning mirror that deflects the light beam in a first predetermined direction and in a second predetermined direction which is perpendicular to the first predetermined direction, and a fixed mirror. In this case, the scanning mirror and the fixed mirror may be mounted on the same transparent substrate.

Further optionally, the probe may include an objective lens, and the objective lens and the transparent substrate are made of the same optical material.

Still optionally, the scanning type confocal probe may be provided with a pin hole that allows light reflected by in-vivo tissues on an object side focal plane of the objective lens to pass through and shields light reflected by the tissues on portions other than the object side focal plane of the objective lens.

In a particular case, the scanning type confocal probe includes a single mode optical fiber that receives and transmits light from the tissues via the objective lens, in which an object lens side end surface of the optical fiber functions as the pin hole.

According to another aspect of the invention, there is provided a confocal endoscope, which includes a surface observing system which allows an observation, via the objective lens, of a surface of in-vivo tissues inside a human cavity at a first magnification, and a confocal observing system which allows an observation, via the objective lens, of a surface image and/or tomogram at a second magnification which is greater than the first magnification.

Optionally, the surface observing system and the confocal observing system have a common objective optical system.

Further, an optical axis of the surface observing system and an optical axis of the confocal observing system substantially coincide with each other at least in the common objective optical system.

In a particular example, the confocal observing system includes an objective optical system, a scanning system that scans the surface and/or section of the tissues to receive light reflected thereat, and a pickup system that selectively transmits the light reflected by the tissues on a focal plane of an objective optical system using a pin hole.

According to a further aspect of the invention, there is provided an endoscope device, which is provided with a light source that emits a light beam for illuminating an object to be observed, a scanning type confocal probe which includes at least one scanning mirror and a transparent substrate on which the at least one scanning mirror is mounted, the transparent substrate being inserted in an optical path of the confocal probe such that a light beam passing along the optical path is deflected by the at least one scanning mirror, and an image reproducing system that reproduces an image of the object using light reflected by the object and passed through the confocal probe.

In a particular case, the endoscope device may include a first scanning mirror that deflects the light beam in a first predetermined direction, and a second scanning mirror that deflects the light beam in a second predetermined direction which is perpendicular to the first predetermined direction. It should be noted that the first scanning mirror and the second scanning mirror may be mounted on the same transparent substrate.

In another case, the endoscope device may include a scanning mirror that deflects the light beam in a first predetermined direction and in a second predetermined direction which is perpendicular to the first predetermined direction, and a fixed mirror. Also in this case, the scanning mirror and the fixed mirror may be mounted on the same transparent substrate.

Optionally, the endoscope device may include an objective lens, and the objective lens and the transparent substrate are made of the same optical material.

According to another aspect of the invention, there is provided an endoscope device, which is provided with a first light source that emits light for illuminating an object to be observed, a second light source that emits a light beam to be scanned to illuminate the object, a surface observing system which allows an observation, via the objective lens, of a surface of in-vivo tissues inside a human cavity at a first magnification, and a confocal observing system which scans the light beam emitted by the second light source, the confocal observing system allowing an observation, via the objective lens, of a surface image and/or tomogram at a second magnification which is greater than the first magnification.

BRIEF DESCRIPTION OF THE ACCOMPANYING DRAWINGS

DESCRIPTION OF THE EMBODIMENTS

Hereinafter, referring to the accompanying drawings, scanning type confocal probes according to embodiments of the invention will be described.

Figure 1:
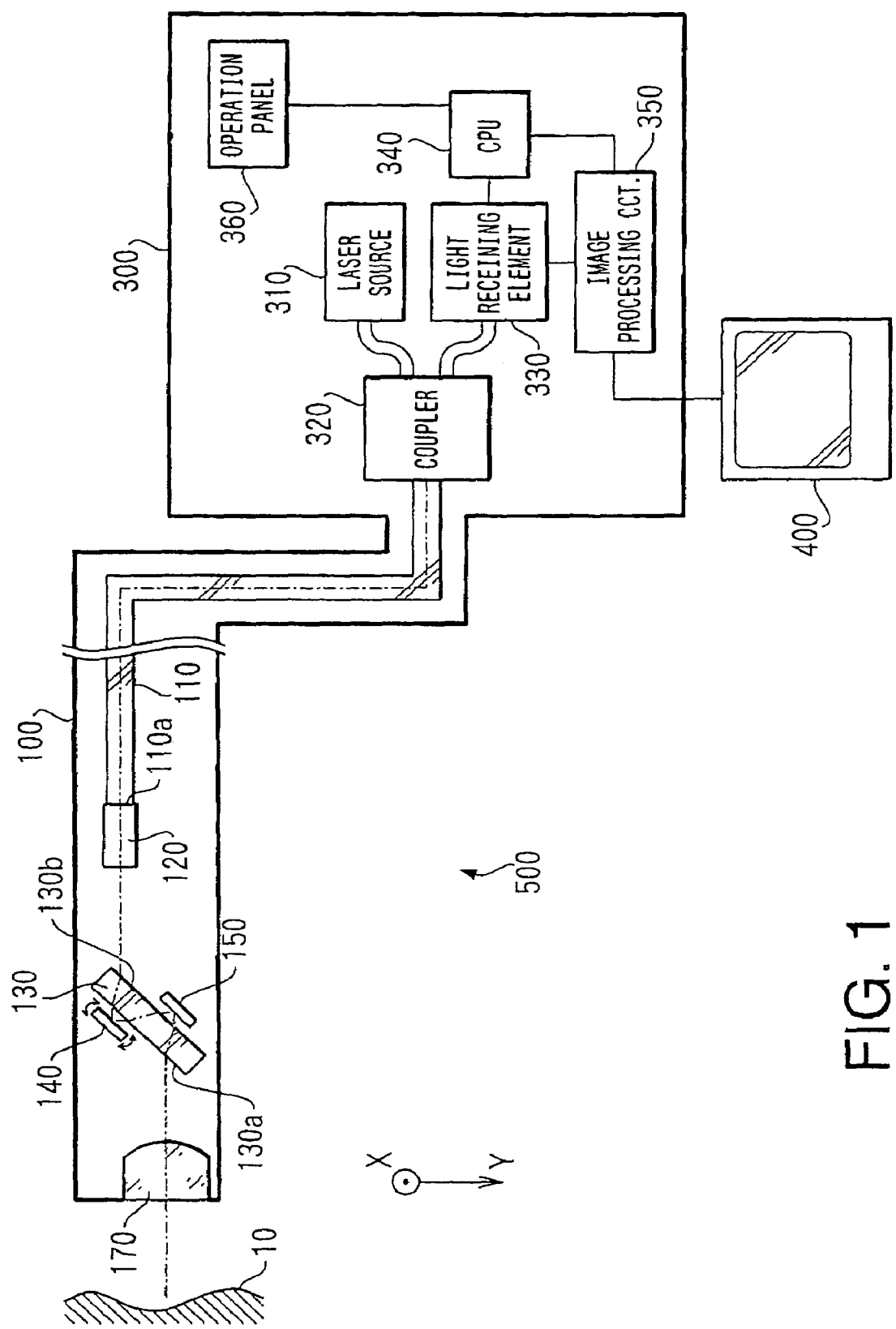
FIG. 1 is a block diagram of a scanning type confocal probe according to a first embodiment of the invention.

FIG. 1 shows a block diagram of a scanning type confocal probe device 500 according to a first embodiment of the invention. The confocal probe device 500 includes a scanning type confocal probe unit 100, a processing unit 300 and a monitor 400.

The confocal probe unit 100 is inserted in a forceps channel of an endoscope (not shown), which is inserted in a human cavity. An image inside the human cavity (e.g., tissues) can be captured using the probe unit 100. The captured image is processed by the processing unit 300 and is displayed on the monitor 400.

As shown in FIG. 1, the processing unit 300 includes a laser source 310, a coupler 320, a light receiving element 330, a CPU (Central Processing Unit) 340, an image processing circuit 350 and an operation panel 360.

The laser source 310 according to the first embodiment emits an He-Ne laser having a wavelength of 421 nm. It is known that the shorter the wavelength of the laser beam is, the higher the resolution of the image is. It should be noted that the laser source 310 is not limited to one that emits the He-Ne laser, and may be one that emits Ar+ laser (488 nm).

The laser beam emitted by the laser source 310 is introduced to the confocal probe unit 100 through the coupler 320.

The confocal probe unit 100 includes, as shown in FIG. 1, an optical fiber 110, a GRIN (Gradual Index) lens 120, a glass substrate 130, micromirrors 140 and 150, and an objective lens 170.

The optical fiber 110 is a single mode fiber, and transmits the laser beam emitted by the processing unit 300 to the GRIN lens 120.

The GRIN lens 120 is a lens that is configured such that the refractive index thereof gradually changes therein. It is known that the GRIN lens enables downsizing of an optical system. The laser beam passed through the optical fiber 110 is incident on the GRIN lens 120, which collimates the laser beam. The collimated laser beam is directed toward the glass substrate 130.

The micromirrors 140 and 150 are mounted on the glass substrate 130. Specifically, the glass substrate 130 has a first surface 130a on which the micromirror 140 is mounted, and a second surface 130b on which the micromirror 150 is mounted. The first surface 130a and the second surface 130b are parallel with each other. The glass substrate 130 is made of glass material such as BK7 or quart glass, which is generally used for optical elements. The glass substrate 130 is arranged such that the first surface 130a and the second surface 130b incline with respect to an optical axis of the probe unit 100 by 45 degrees, and the laser beam emitted from the GRIN lens 120 is reflected by the micromirror 140, then reflected by the micromirror 150 and is incident on the objective lens 170. It should be noted that the inclination angle (45 degrees) of the first and second surfaces 130a and 130b with respect to the optical axis described above is an example, and can be changed depending on various conditions such as an refractive index of the glass substrate 130 and a space inside the probe unit 100.

Figure 2:
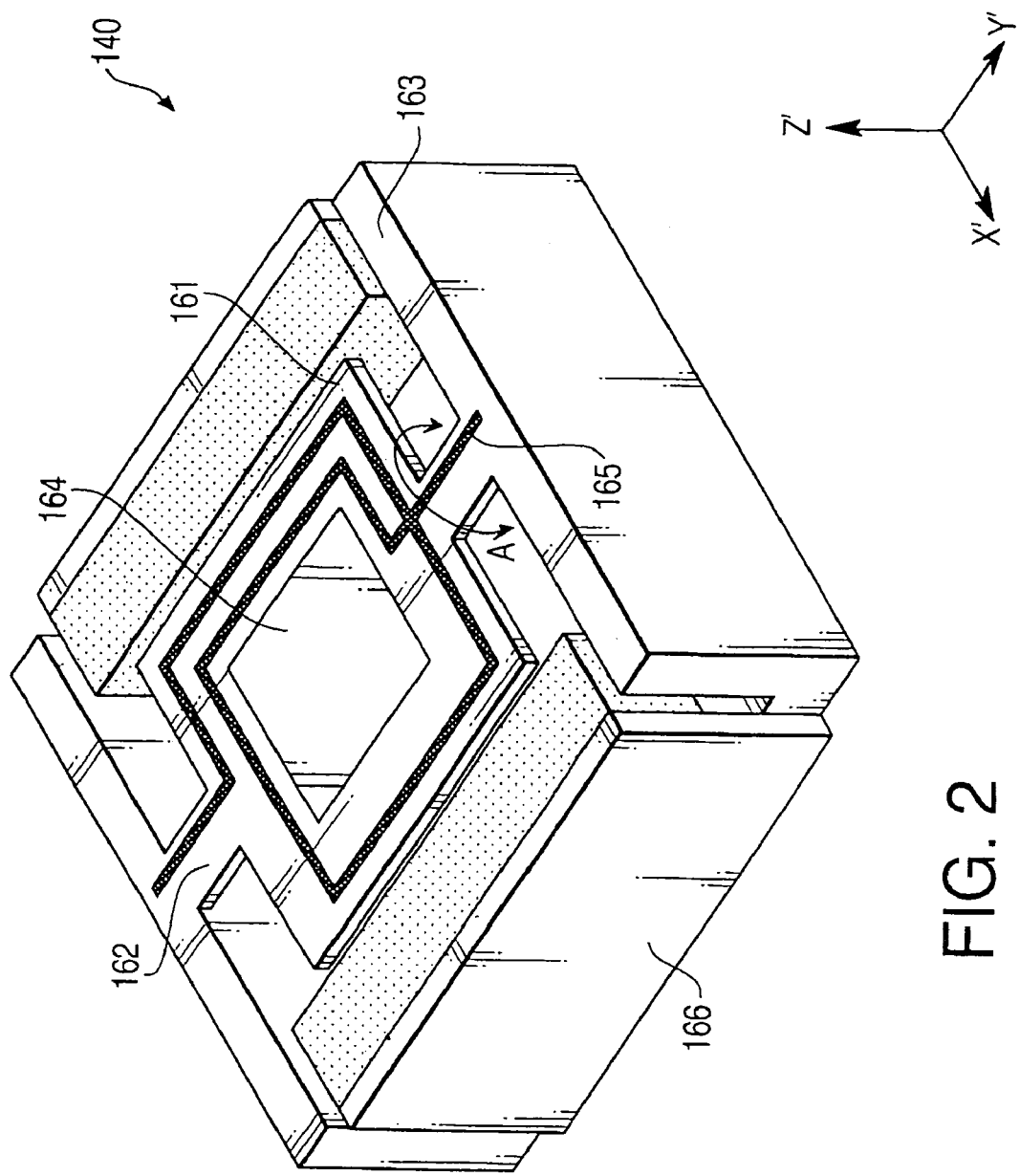
FIG. 2 is a perspective view of a micromirror employed in the confocal probe in each embodiment.

FIG. 2 is a perspective view of the micromirror 140. Since the micromirror 150 has the same structure of the micromirror 140, only the micromirror 140 will be described. The micromirror 140 includes a plate member 161, torsion bars 162 and a supporting frame 163, which are formed integrally by etching a silicon plate. The plate member 161 is provided with a mirror section 164 which is formed, for example, by evaporating reflective material (e.g., aluminum, gold or dielectric multilayer). Further, on an upper surface of the micromirror 140 (i.e., on upper surfaces of the plate member

161, torsion bars 162 and the supporting frame 163), a planar coil 165 formed of a thin copper layer is provided. A pair of yoke units 166, each having a permanent magnet and a yoke, are arranged to extend in a longitudinal direction of the torsion bars 162.

The yoke units 166 generate a magnetic field in a direction substantially parallel with the plate member 161 and substantially perpendicular to the longitudinal direction of the torsion bars 162 (i.e., in X' direction in FIG. 2). When an electrical current is supplied to the planar coil 165, driving forces (torque) that are parallel with the Z' direction and opposite to each other are generated at sides of the plate member 161 extending in Y' direction in accordance with Fleming's left hand law. The quantity of the torque is substantially proportional to the electrical current supplied to the planar coil 165.

In accordance with the generated torque, the plate member 161 rocks in a direction indicated by arrow A in FIG. 2. Since the plate member 161 and the torsion bars 162 are formed integrally, as the plate member 161 rotates, the torsion bars 162 are twisted, which generates elastically reactive force. With this mechanism, the plate member 161 rotates until the torque and the reactive force balance. When the plate member 161 is located at a position where the torque and the reactive force balance, the plate member 161 stops rotating and stays the balance position.

The micromirror 140 and the micromirror 150 are mounted on the glass substrate 130 such that torsion bars 162 of the micromirror 140 and the torsion bars 162 of the micromirror 150 are oriented orthogonally to each other. When the plate member 161 of the micromirror 140 rotates, the laser beam scans in an X-direction (see FIG. 1). When the plate member 161 of the micromirror 150 rotates, the laser beam scans in the Y-direction (see FIG. 1). As shown in FIG. 1, the X direction and Y direction are perpendicular to the optical axis of the probe unit 100, and are parallel with a surface 10 to be examined.

Although not shown, each of the micromirrors 140 and 150 has a pair of detection coils on an opposite side of the surface of the plate member 161 formed with the planar coil 165. The electrical current supplied to the planar coil 165 includes a driving current for rotating the plate member 161, and an AC current for detecting the displacement angle (i.e., a rotation angle) of the plate member 161. As the AC current flows through the planar coil 165, due to mutual inductance between the planar coil 165 and the detection coils, induced voltages are generated across each detection coil.

If the pair of detection coils are arranged at the same distance with respect to the planar coil 165 at opposite sides, when the plate member 161 is in its neutral state (no torque is generated), a difference of the induced voltages is zero. When an electrical current is supplied and the plate member 161 rotates, one of the pair of coils becomes closer to the planar coil 165, while the other becomes apart from the planar coil 165. Therefore, a difference occurs between the voltages induced in the pair of detection coils. By detecting the difference of the induced voltages, the displaced angle (i.e., the rotation angle) of the micromirror can be detected.

The collimated laser beam directed toward the micromirror 140 emerges from the first surface 130a, is reflected by the micromirror 140 and is incident on the first surface 130a. The laser beam proceeds toward the micromirror 150. That is, the laser beam emerges from the second surface 130b, is reflected by the micromirror 150, and is incident on the second surface 130b again. The laser beam then emerges from the first surface 130a and is directed to the objective lens 170.

The objective lens is formed of glass material similar to the glass substrate 130 (e.g., BK7 or quart glass). The collimated laser beam emerged from the first surface 130a is converged on the surface or at a certain depth of the target portion 10 to be examined.

The light beam incident on the target portion 10 is reflected thereat, the reflected light being incident on the objective lens 170. If the light is reflected at the focal point of the objective lens 170, the light reflected by the target area and entered the objective lens 170 is collimated by the objective lens 170. Then, the light returns the path along which the emerging beam proceeded to the target portion 10. The reflected light is then incident on the GRIN lens 120.

As described above, the optical fiber 110 is the single mode fiber. Therefore, the diameter of the core is very small, ranging from 3 to 9 μm (which varies depending on the working wavelength). An end surface 110a of the optical fiber 110 is located at a position which is conjugate with the focal point on the object side of the objective lens 170. Thus, among the light flux incident on the target portion 10, those converged on the target portion 10 is converged by the GRIN lens 120 on the end surface 110a of the optical fiber 110. The light flux converged on the end surface 110a is transmitted through the core of the optical fiber 110, and received by the light receiving element 330 through the coupler.

The reflected light that is reflected on surfaces of the target portion 10 other than the focal plane of the objective lens 170 is not converged on the end surface 110a, and thus does not enter the core of the optical fiber 110. Accordingly, such light is not transmitted to the processing unit 300. That is, the optical fiber 110 transmits only the light reflected by the target plane 10 on the focal plane of the objective lens 170 to the processing unit 300. Thus, the end surface 110a of the optical fiber 110 functions as a pin hole which shields the light reflected by surfaces other than the focal plane of the objective lens 170, and functions to allow the image obtained by the optical system provided to the confocal probe unit 100 to the processing unit 300.

Further, an aperture stop (i.e., a pin hole) is provided on a focal plane of the GRIN lens 120, and the optical system inside the probe unit 100 is a telecentric optical system, which has little loss of light amount.

The light beam received by the light receiving element 330 is converted into electrical signals corresponding to the received light amount (i.e., image signals), which is transmitted to the image processing circuit 350. The image processing circuit applies predetermined image processing and generates video signals such as a composite video signal, an RGB signal, or an S-video signal. The video signal is applied to the monitor 400, thereby an image of the target portion 10 on the focal plane of the objective lens 170, which image is captured by the probe unit 100, is displayed.

By operating the operation panel 360 of the processing unit 300, an operator can selectively observe the images captured by the confocal probe unit 100.

Specifically, when the operator operates the operation panel 360, signals corresponding to the operation are transmitted to the CPU 340. Then, the CPU 340 drives the micromirror 140 and the micromirror 150 so that the laser beam scans the target portion 10 in the X direction and the Y direction. The reflected light on the focal plane of the objective lens 170 is transmitted to the processing unit 300 as described above.

It should be noted that, by varying a moving (scanning) range of the micromirror 140 and/or micromirror 150, a field of view of an observing image can be varied with ease. That is, when the scanning range is smaller, an image in a small observing field is obtained, while when the scanning range is larger, an image within a wide area can be obtained.

Figure 3:
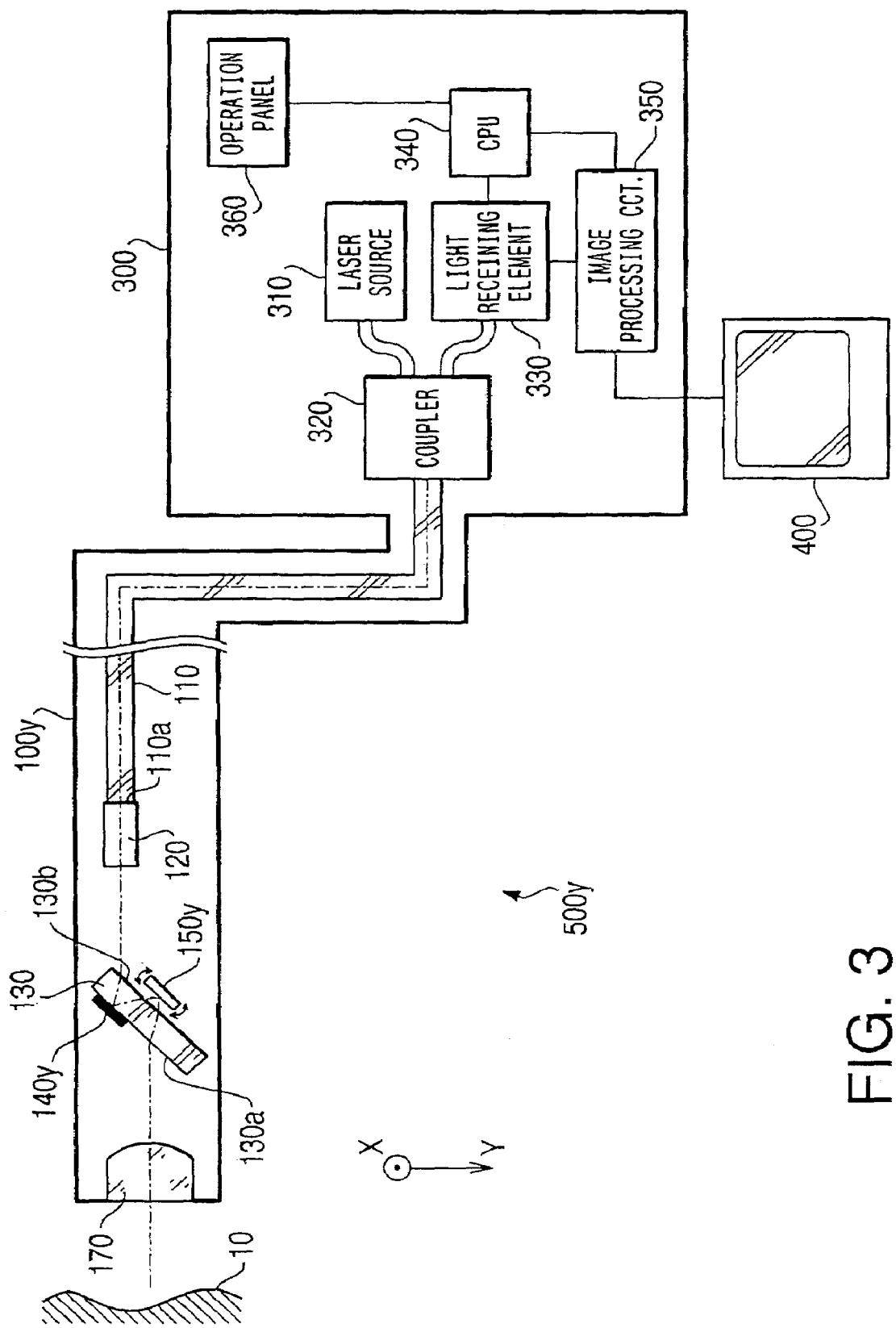
FIG. 3 is a block diagram of a scanning type confocal probe according to a second embodiment of the invention.

FIG. 3 is a block diagram showing a confocal probe device 500$y$ according to a second embodiment of the invention. In FIG. 3, the elements identical to those shown in FIG. 1 are given the same reference numerals, and description thereof will not be repeated.

The confocal probe device 500$y$ includes a confocal probe unit 100$y$, the processing unit 300 and the monitor 400.

According to the confocal probe device 500$y$, only one micromirror is used to obtain a two-dimensional image of the tissues. In the confocal probe device 500$y$, a two-axis scanning type (which is capable of deflecting the laser beam both in the X direction and in the Y direction) micromirror 150$y$ is employed instead of the second micromirror 150 of the first embodiment. Further, the first micromirror 140 of the first embodiment is replaced with a mirror (e.g., a single metal layer or multilayer coating of dielectric substance) 140$y$.

It should be noted that, in the structure shown in FIG. 3, the mirror 140$y$ is formed on the first, surface 130$a$ and the micromirror 150$y$ is mounted on the second surface 130$b$. This can be reversed, that is, the mirror may be formed on the second surface 130$b$ and the two-axis scanning type micromirror may be mounted on the first surface 130$a$.

Figure 4:
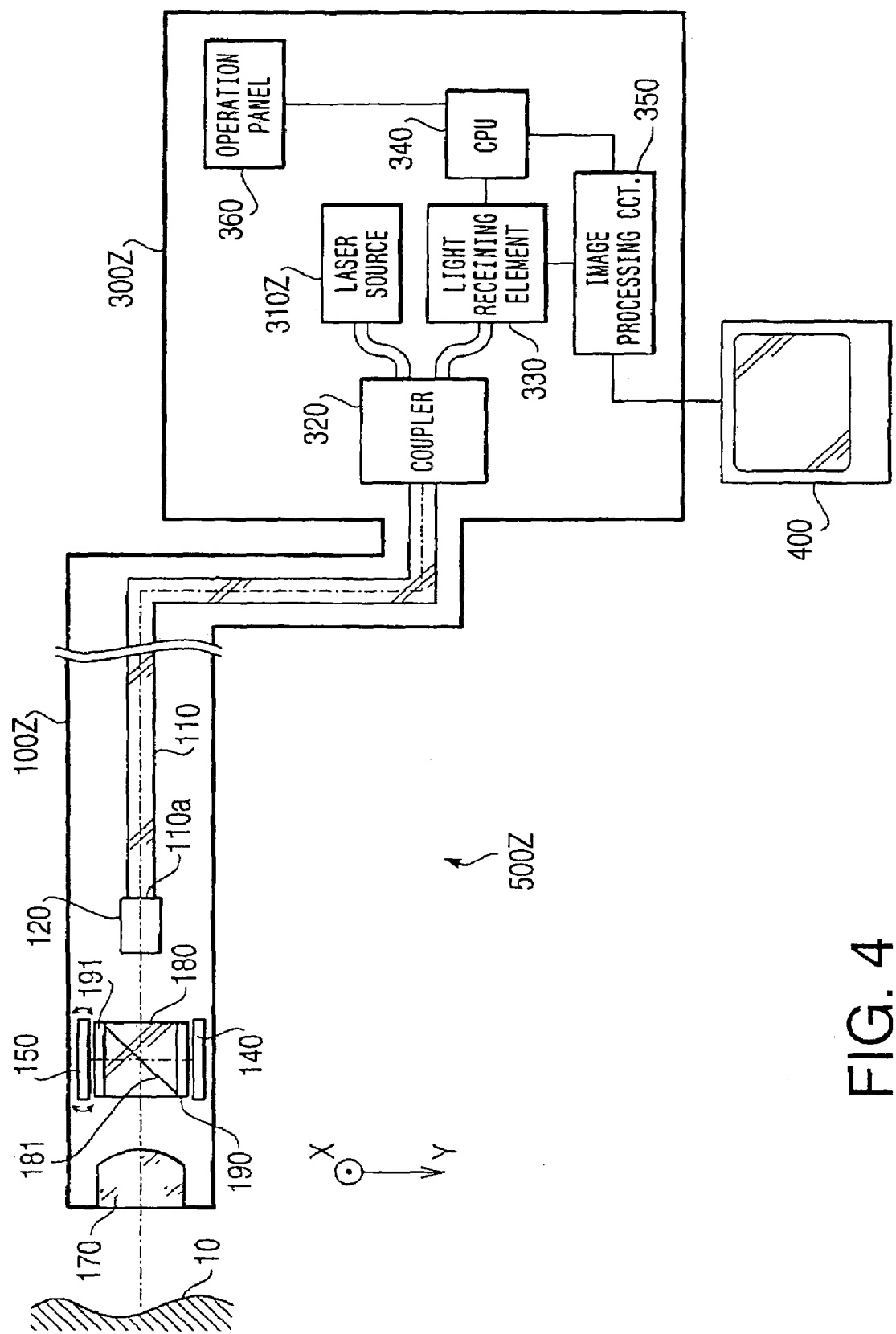
FIG. 4 is a block diagram of a scanning type confocal probe according to a third embodiment of the invention.

FIG. 4 is a block diagram showing a confocal probe device 500$z$ according to a third embodiment of the invention. In FIG. 4, the elements identical to those shown in FIG. 1 are given the same reference numerals, and description thereof will not be repeated.

As shown in FIG. 4, the confocal probe device 500$z$ includes a confocal probe unit 100$z$, a processing unit 300$z$ and the monitor 400.

The processing unit 300$z$ includes a laser source 310$z$ having a Brewster window, through which polarized beam is emitted. The beam emerged from the Brewster window is an S-polarized beam with respect to a polarization layer 181, which will be described later.

The laser beam emitted by the laser source 310Z is incident on the optical fiber 110 of the confocal probe unit 100$z$ through the coupler 320. The light beam transmitted through the optical fiber 110 is collimated by the GRIN lens 120 and is introduced to a polarization beam splitting cube 180.

The polarization beam splitting cube 180 has a polarization layer 181, which is arranged to form an angle of 45 degrees with respect to the optical axis of the probe unit 100$z$. The polarization layer 181 reflects the S-polarization beam and transmits the P-polarization beam.

On surfaces of the polarization beam splitting cube 180 perpendicular to the optical axis of the probe unit 100$z$, $\lambda/4$ plate 190 and $\lambda/4$ plate 191 are formed, respectively. The $\lambda/4$ plates function to convert linear polarization light into circular polarization light, and convert the circular polarization light into the linear polarization light.

The S-polarization beam emitted by the laser source 310$z$ is directed to the GRIN lens 120 through the coupler 320 and the optical fiber 110. The GRIN lens 120 collimates the incident beam. The collimated S-polarized beam is incident on the polarization layer 181, and reflected thereby to proceed toward the $\lambda/4$ plate 190. The beam passes the $\lambda/4$ plate, thereby the S-polarization beam being converted into the circular polarization beam and incident on the micromirror 140.

The beam is then reflected by the micromirror 140 and passes through the $\lambda/4$ plate 190 again, thereby the circular polarization beam being converted into a P-polarized beam.

Since the polarization layer 181 allows the P-polarization beam to pass therethrough, the beam reflected by the micromirror 140 and passed through the $\lambda/4$ plate 190 passes through the polarization layer 181 and incident on the $\lambda/4$ plate 191. The beam is converted into the circular polarization beam and is reflected by the micromirror 150. The reflected beam passes through the $\lambda/4$ plate 191 again, thereby it is converted to the S-polarization beam and incident on the polarization layer 181. Since the beam is the S-polarization beam, it is reflected by the polarization layer 181, and is directed to the objective lens 170 as shown in FIG. 4. The beam, which is a collimated beam, is converged by the objective lens 170 on the target portion 10 on the surface thereof or at a predetermined depth.

The beam reflected on the target portion 10 returns the same path as described above, and enters the GRIN lens 120. Similarly to the first embodiment, only the light reflected on the focal plane of the objective lens 170 is transmitted to the processing unit 300$z$. The reflected light is received by the light receiving element 330, which generates an image signal. The image signal is then processed in the image processing circuit 350 and a focused image is displayed on the monitor 400.

It should be noted that, according to the third embodiment, even if a position of the polarization beam splitting cube 180 with respect to the probe unit 100$z$ is varied, the optical axis of the GRIN lens 120 and the optical axis of the objective lens 170 are maintained to coincide with each other. Therefore, accurate imaging can be ensured.

Similar to the second embodiment, one of the micromirrors 140 and 150 of FIG. 4 can be replaced with a two-axis type micromirror and the other can be replaced with a mirror.

Figure 5:
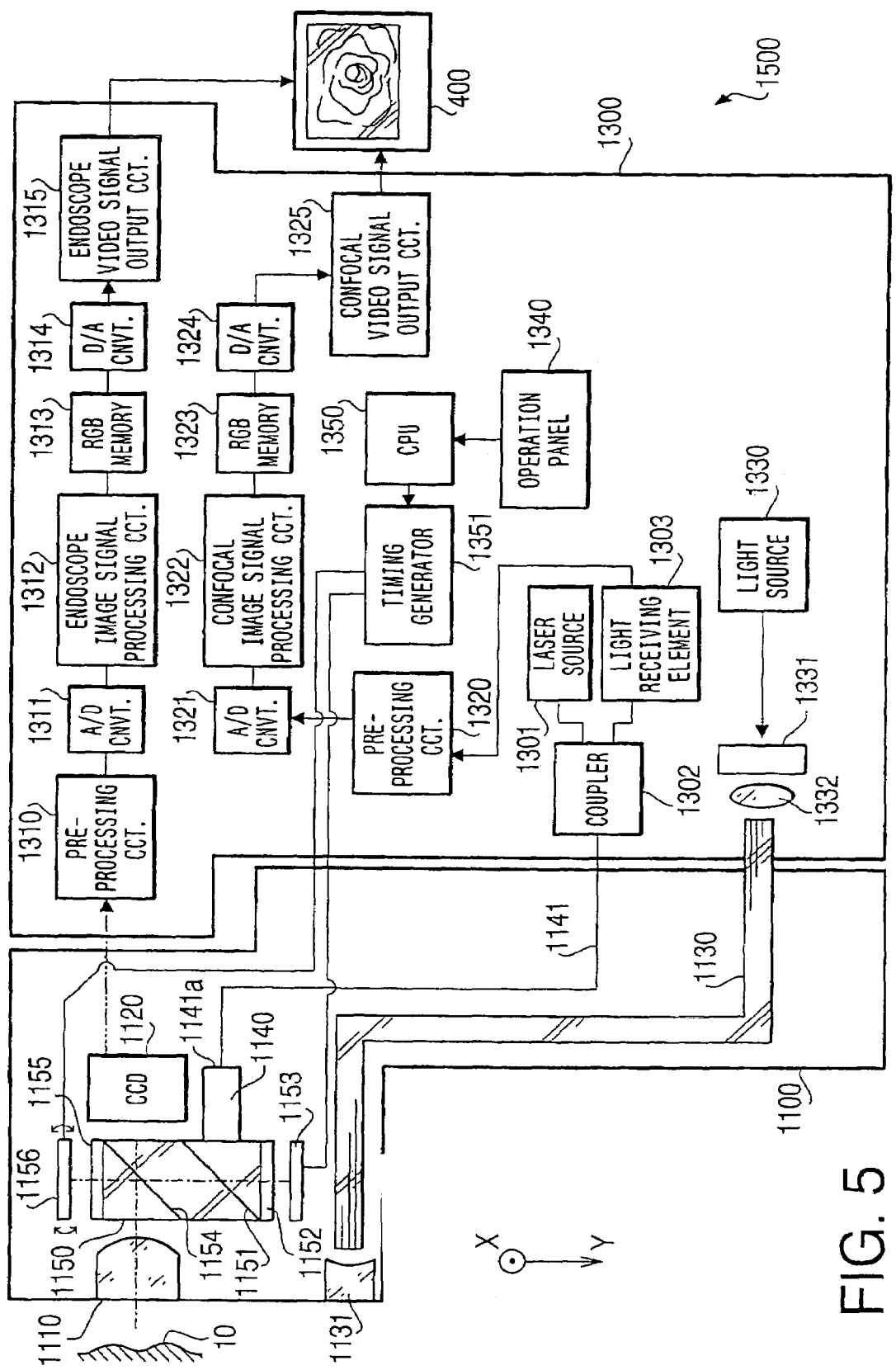
FIG. 5 is a block diagram of a scanning type confocal endoscope according to a fourth embodiment of the invention.

FIG. 5 is a block diagram showing a confocal endoscope device 1500 according to a fourth embodiment of the invention. The confocal endoscope device 1500 includes a confocal endoscope 1100, a processing unit 1300 and the monitor 400.

The confocal endoscope 1100 includes a surface observing section for observing inside the human cavity with a relatively wide field of view. The surface observing section includes an objective lens 1110, a CCD (Charge Coupled Device) 1120, a light guide 1130 and a projection lens 1131.

According to the embodiment, a color image is obtained in accordance with a frame sequential method. The processing unit 1300 has an RGB rotatable filter unit 1331, which is inserted in an optical path of a light source 1330. The RGB filter unit 1331 has filters of R (red), G (green) and B (blue). The RGB filter unit 1331 is rotated to locate the RGB filters sequentially in the optical path. The light passed through the RGB filter unit 1331 is converged by a converging lens 1332, transmitted through the light guide 1130, and directed to the target portion 10 through the projection lens 1131. With this configuration, the target portion 10 is illuminated with the light passed through RGB filters, sequentially.

The CCD 1120 captures an image of the target portion 10 illuminated with RGB light via the objective lens 1110 and a polarization unit 1150, sequentially to obtain images of respective color components, which are combined to generate a color image by the processing unit 1300.

The CCD 1120 outputs image signals corresponding to the captured images of the target portion 10. The image signals are transmitted to a pre-processing circuit 1310 of the processing unit 1300. The pre-processing circuit 1310 amplifies the received image signals and applies a sampling/holding process. The image signals are then transmitted to an A/D (analog to digital) converter 1311.

The A/D converter 1311 converts the received image signals (which are analog signals) to digital signals. The digital signals are divided by the endoscope image signal processing circuit 1312, in synchronism with switching of the RGB filter unit 1331, into R component signal, G component signal, and B component signal, which are stored in an RGB memory 1313.

The RGB memory 1313 has three frame memories for the RGB components, and stores the separated color image signals in the respective frame memories. The thus stored image signals are readout simultaneously, converted into analog signals by a D/A converter 1314, and transmitted to an endoscope video signal output circuit 1315.

The endoscope video signal output circuit 1315 converts the transmitted analog signal into an RGB video signal, a composite video signal or an S-video signal, which is transmitted to the monitor 400. With this configuration, the image of the target portion 10 in a relatively wide area is displayed.

It should be noted that, in the fourth embodiment, the color CCD image is obtained in accordance with the frame sequential method. The invention need not be limited to this configuration, and a color CCD may also be used for capturing a color image. In such a case, the target portion 10 is illuminated with white light.

The confocal endoscope 1100 further includes a confocal observing section for observing a surface image or tomography inside the human cavity at a relatively large magnification. The confocal observing section includes a GRIN lens 1140, an optical fiber 1141, the polarization unit 1150, a micromirror 1153 and a micromirror 1156.

The processing unit 1300 includes a laser source 1301, which emits a He-Ne laser beam having a wavelength of 632 nm. It should be noted that, when a laser source that emits a laser beam having a shorter wavelength, a higher resolution of the image can be achieved. Thus, the laser source 1301 need not be limited to the He-Ne laser, but an Argon ion laser may be used instead.

Further, according to the fourth embodiment, the laser source 1301 has a Brewster window. The laser source 1301 emits an S-polarization laser beam with respect to the polarization layer 1151. The laser beam emitted by the laser source 1301 is transmitted through the optical fiber 1141, which is a single mode fiber, via a coupler 1302.

The laser beam emerged from the optical fiber 1141 is incident on the GRIN lens 1140, which collimates the laser beam. The collimated laser beam emerges from the GRIN lens 1140 toward the polarization layer 1151 included in the polarization unit 1150.

The polarization unit 1150 is formed such that two polarization beam splitting cubes are cemented. The two polarization beam splitting cubes include a polarization layer 1151 and a polarization layer 1154, each of which is configured to reflect an S-polarization beam and allows the P-polarization beam to pass through. Further, on a pair of surfaces parallel to the optical axis of the confocal endoscope 1100 and opposite to each other, $\lambda/4$ plates 1152 and 1155 are cemented. Each of the $\lambda/4$ plates 1152 and 1155 converts a linear polarization beam into a circular polarization beam, and the circular polarization beam into the linear polarization beam.

The collimated beam emerged from the GRIN lens 1140 and incident on the polarization layer 1151 as the S-polarized beam reflected by the polarization layer 1151 by 90 degrees and proceeds toward the $\lambda/4$ plate 1152. The beam then passes through the $\lambda/4$ plate 1152 and incident on the micromirror 1153 as the circular polarization beam.

The circular polarization collimated beam incident on the micromirror 1153 is reflected thereby, passes through the $\lambda/4$ plate 1152 again, and incident on the polarization layer 1151 as the P-polarized collimated beam. Since the polarization layer 1151 allows the P-polarized beam to pass therethrough, the beam is incident on the polarization layer 1154 as the P-polarization beam, passes through the polarization layer 1154, and incident on the $\lambda/4$ plate 1155.

The P-polarized collimated beam incident on the $\lambda/4$ plate 1155, passes therethrough, and incident on the micromirror 1156 as the circular polarization beam. The beam is then reflected by the micromirror 1156, passes through the $\lambda/4$ plate 1155, and incident on the polarization layer 1154 as the S-polarization collimated beam.

Since the polarization layer 1154 reflects the S-polarization beam, as described above, it proceeds toward the objective lens 1110. The optical axis of the confocal probe section and the optical axis of the surface observing section coincide with each other. The collimated beam is converged on the target portion 10 via the objective lens 1110. With this configuration, since the surface observing section and the confocal probe section use the same objective lens to view the target portion 10, no parallax occurs between the images obtained by the two optical systems.

The laser beam incident on the target portion 10 is reflected thereby and incident on the objective lens 1110. The objective lens 1110 collimates the reflected beam, which returns the optical path as described above and enters the GRIN lens 1140.

As described above, the optical fiber 1141 is the single mode fiber. Therefore, the diameter of the core is very small, ranging from 3 to 9 μm (which varies depending on the working wavelength). An end surface 1141*a* of the optical fiber 1141 is located at a position which is conjugate with the focal point on the object side of the objective lens 1110. Thus, among the light flux incident on the target portion 10, those converged on the target portion 10 is converged by the GRIN lens 1140 on the end surface 1141*a* of the optical fiber 1141. The light flux converged on the end surface 1141*a* is transmitted through the core of the optical fiber 1141, and received by the light receiving element 1303 through the coupler 1302.

The reflected light that is reflected on surfaces of the target portion 10 other than the focal plane of the objective lens 1110 is not converged on the end surface 1141*a*, and thus does not enter the core of the optical fiber 1141. Accordingly, such light is not transmitted to the processing unit 1300. That is, the optical fiber 1141 transmits only the light reflected by the target plane 10 on the focal plane of the objective lens 1110 to the processing unit 1300. Thus, the end surface 1141*a* of the optical fiber 1141 functions as a pin hole which shields the light reflected by surfaces other than the focal plane of the objective lens 1110, and functions to allow the image obtained by the optical system provided to the confocal endoscope device 1500 to the processing unit 1300.

Further, an aperture stop (i.e., the pin hole) is provided on a focal plane of the GRIN lens 1140, and thus the optical system inside the endoscope device 1500 is a telecentric optical system, which has little loss of light amount.

The light beam received by the light receiving element 1303 is converted into electrical signals corresponding to the received light amount (i.e., image signals), which is transmitted to a pre-processing circuit 1320. The pre-processing circuit 1320 amplifies the received signal and applies sampling/holding procedure. Then, the output signal of the pre-processing circuit 1320 is input to an A/D converter

1321, which converts the input image signal (analog) to a digital signal and transmits the converted signal to a confocal image signal processing circuit 1322. The confocal image signal processing circuit 1322 is divided into R, G and B component signals in accordance with the rotation of the RGB filter unit 1331, and the R, G and B component signals are stored in an RGB memory 1323. The thus stored image signals are read out at predetermined timing, converted into analog signals by a D/A converter 1324, and transmitted to a confocal video signal processing circuit 1325. The confocal video signal output circuit 1325 generates video signals such as a composite video signal, an RGB signal, or an S-video signal. The video signal is applied to the monitor 400, thereby an image of the target portion 10 on the focal plane of the objective lens 1110, which is captured by the confocal image pickup section, is displayed at a high magnification on the monitor 400.

By operating an operation panel 1340 of the processing unit 1300, an operator can selectively observe the images captured by the confocal endoscope 1100.

Specifically, when the operator operates the operation panel 1340, signals corresponding to the operation are transmitted to a CPU 1350. Then, the CPU 1350 controls a timing generator 1351 in accordance with the received signal.

The timing generator 1351 drives, under control of the CPU 1350, the micromirror 1153 and the micromirror 1156 so that the laser beam scans the target portion 10 in the X direction and the Y direction. The reflected light on the focal plane of the objective lens 1110 is transmitted to the processing unit 1300 as described above.

It should be noted that, by varying a moving (scanning) range of the micromirror 1153 and/or micromirror 1156, a field of view of an observing image can be varied with ease. That is, when the scanning range is smaller, an image in a small observing field is obtained, which is displayed at a large magnification, while when the scanning range is larger, an image within a wide area can be obtained, which is displayed at a lower magnification. That is, without a zooming optical system which typically includes a plurality of groups and numbers of lenses, the magnification of the displayed image can be changed. Since the zooming optical system is unnecessary, the entire size of the confocal endoscope device can be made relatively compact.

According to the fourth embodiment, the operator can select a display method of the images on the monitor 400 by operating the operation panel 1340. For example, the operator can switch between the entire image of the target portion 10 using the surface observation section, and the image captured by the confocal pickup section. Alternatively, the entire display area of the monitor 400 is divided and both the images obtained by the surface observation section and the confocal pickup section may be displayed. Since the field of view of the surface observation section is relatively wide, it can be used as a finder system for the confocal pickup section.

In the above-described fourth embodiment, only one monitor is employed. This configuration may be modified such that two or more monitors are provided and the image captured by the surface observation system (CCD) and the image captured by the confocal pickup system are displayed in different monitors.

Conventionally, endoscopes provided with a zooming system have been used. Typically, the conventional zooming system electronically increases the magnification of the image. Therefore, when the magnification is raised, the quality of the image becomes worse. The operator is required to treat the target portion with observing such an image having a worse quality. Thus, the operator should be especially skilled in operating such an endoscope.

As an alternative, endoscopes provided with an optical zooming system have been suggested. However, in such an endoscope, a zooming optical system should be provided at the distal end portion of the endoscope, which increases the diameter of the endoscope. Further, in such a system, an image at a large magnification and an image at a low magnification cannot be observed simultaneously.

According to the fourth embodiment, it becomes possible to obtain a large magnification image without lowering the image quality. Further, images at the large magnification and the low magnification can be observed simultaneously, or at least such images are quickly switched. Therefore, operability is excellently improved, and the target portion can be treated safely and quickly.

The fourth embodiment may be modified such that the image of the wide area is observed directly with the operator's eye without using the image capturing element (CCD).

In the above-described embodiments, in order to illuminate the target portion, the He-Ne laser is used. The invention is not limited to this configuration, and another light having a relatively short wavelength may be used. For example, an ultra-high-pressure mercury lamp, which emits short-wavelength light including near ultraviolet light, may be used as the light source. In such a case, it becomes possible to observe fluorescent light image of the target portion.

What is claimed is:

1. A scanning type confocal probe, comprising:
   at least one scanning mirror; and
   a transparent substrate on which said at least one scanning mirror is mounted, said transparent substrate being inserted in an optical path of said confocal probe such that a light beam passing along the optical path is deflected by said at least one scanning mirror,
   wherein said at least one scanning mirror comprises a first rotating scanning mirror that deflects the light beam in a first predetermined direction, and a second rotating scanning mirror that deflects the light beam in a second predetermined direction perpendicular to the first predetermined direction, said first rotating scanning mirror and said second rotating scanning mirror being rotatably mounted with respect to the transparent substrate.

2. The scanning type confocal probe according to claim 1, further including an objective lens, said objective lens and said transparent substrate being made of the same optical material.

3. The scanning type confocal probe according to claim 2, further comprising a pin hole that allows light reflected by in-vivo tissues on an object side focal plane of said objective lens to pass through and shields light reflected by the tissues on portions other than the object side focal plane of said objective lens.

4. The scanning type confocal probe according to claim 3, further comprising a single mode optical fiber that receives and transmits light from the tissues via said objective lens, an object lens side end surface of said optical fiber functioning as the pin hole.

5. A scanning type confocal probe, comprising:
   at least one scanning mirror; and
   a transparent substrate on which said at least one scanning mirror is mounted, said transparent substrate being inserted in an optical path of said confocal probe such that a light beam passing along the optical path is deflected by said at least one scanning mirror, wherein said at least one scanning mirror includes:
a scanning mirror that deflects the light beam in a first predetermined direction and in a second predetermined direction perpendicular to the first predetermined direction; and
a fixed mirror,
said scanning mirror and said fixed mirror being mounted on the transparent substrate.

6. The scanning type confocal probe according to claim 5, further including an objective lens, said objective lens and said transparent substrate being made of the same optical material.

7. The scanning type confocal probe according to claim 6, further comprising a pin hole that allows light reflected by in-vivo tissues on an object side focal plane of said objective lens to pass through and shields light reflected by the tissues on portions other than the object side focal plane of said objective lens.

8. The scanning type confocal probe according to claim 7, further comprising a single mode optical fiber that receives and transmits light from the tissues via said objective lens, an object lens side end surface of said optical fiber functioning as the pin hole.

9. An endoscope device, comprising:
a light source that emits a light beam for illuminating an object to be observed;
a scanning type confocal probe which includes at least one scanning mirror and a transparent substrate on which said at least one scanning mirror is mounted, said transparent substrate being inserted in an optical path of said confocal probe such that a light beam passing along the optical path is deflected by said at least one scanning mirror, said at least one scanning mirror comprises a first rotating scanning mirror that deflects the light beam in a first predetermined direction, and a second rotating scanning mirror that deflects the light beam in a second predetermined direction perpendicular to the first predetermined direction, said first rotating scanning mirror and said second rotating scanning mirror being rotatably mounted with respect to the transparent substrate; and
an image reproducing system that reproduces an image of the object using light reflected by the object and passed through said confocal probe.

10. The endoscope device according to claim 9, further including an objective lens, said objective lens and said transparent substrate being made of the same optical material.

11. The scanning type confocal probe according to claim 10, further comprising a pin hole that allows light reflected by in-vivo tissues on an object side focal plane of said objective lens to pass through and shields light reflected by the tissues on portions other than the object side focal plane of said objective lens.

12. The scanning type confocal probe according to claim 11, further comprising a single mode optical fiber that receives and transmits light from the tissues via said objective lens, an object lens side end surface of said optical fiber functioning as the pin hole.

13. An endoscope device, comprising:
a light source that emits a light beam for illuminating an object to be observed;
a scanning type confocal probe which includes at least one scanning mirror and a transparent substrate on which said at least one scanning mirror is mounted, said transparent substrate being inserted in an optical path of said confocal probe such that a light beam passing along the optical path is deflected by said at least one scanning mirror; and
an image reproducing system that reproduces an image of the object using light reflected by the object and passed through said confocal probe,
wherein said at least one scanning mirror includes:
a scanning mirror that deflects the light beam in a first predetermined direction and in a second predetermined direction perpendicular to the first predetermined direction; and
a fixed mirror,
said scanning mirror and said fixed mirror being mounted on the transparent substrate.

14. The scanning type confocal probe according to claim 13, further including an objective lens, said objective lens and said transparent substrate being made of the same optical material.

15. The scanning type confocal probe according to claim 14, further comprising a pin hole that allows light reflected by in-vivo tissues on an object side focal plane of said objective lens to pass through and shields light reflected by the tissues on portions other than the object side focal plane of said objective lens.

16. The scanning type confocal probe according to claim 15, further comprising a single mode optical fiber that receives and transmits light from the tissues via said objective lens, an object lens side end surface of said optical fiber functioning as the pin hole.

* * * * *

UNITED STATES PATENT AND TRADEMARK OFFICE
CERTIFICATE OF CORRECTION

PATENT NO. : 7,252,634 B2 Page 1 of 1
APPLICATION NO. : 10/699699
DATED : August 7, 2007
INVENTOR(S) : Rogerio Jun Mizuno It is certified that error appears in the above-identified patent and that said Letters Patent is hereby corrected as shown below:

On the Title page, in Item (12), "Mizumo" should be changed to -- Mizuno --; and On the Title page, in Item (75), "Rogerio Jun Mizumo" should be changed to -- Rogerio Jun Mizuno --.

Signed and Sealed this

Twelfth Day of January, 2010

David J. Kappos
*Director of the United States Patent and Trademark Office*